United States Patent
Dholakia et al.

(10) Patent No.: US 9,683,209 B2
(45) Date of Patent: Jun. 20, 2017

(54) MICROFLUIDIC PHOTOPORATION

(75) Inventors: Kishan Dholakia, Fife (GB); Robert Marchington, Fife (GB); Yoshihiko Arita, Fife (GB); Frank Gunn-Moore, St Andrews (GB)

(73) Assignee: UNIVERSITY COURT OF THE UNIVERSITY OF ST ANDREWS, St Andrews (GB)

( * ) Notice: Subject to any disclaimer, the term of this patent is extended or adjusted under 35 U.S.C. 154(b) by 263 days.

(21) Appl. No.: 14/110,384

(22) PCT Filed: Jun. 20, 2012

(86) PCT No.: PCT/GB2012/000537
§ 371 (c)(1),
(2), (4) Date: Nov. 19, 2013

(87) PCT Pub. No.: WO2012/175918
PCT Pub. Date: Dec. 27, 2012

(65) Prior Publication Data
US 2014/0073027 A1    Mar. 13, 2014

(30) Foreign Application Priority Data
Jun. 21, 2011 (GB) .................................. 1110454.4

(51) Int. Cl.
*C12M 1/00* (2006.01)
*C12M 3/00* (2006.01)
(Continued)

(52) U.S. Cl.
CPC ....... *C12M 35/02* (2013.01); *B01L 3/502715* (2013.01); *C12N 13/00* (2013.01);
(Continued)

(58) Field of Classification Search
CPC ....... C12M 35/00; C12M 35/02; C12M 35/06
See application file for complete search history.

(56) References Cited

U.S. PATENT DOCUMENTS 5,423,513 A    6/1995    Chervet et al.
5,444,807 A    8/1995    Liu
(Continued)

FOREIGN PATENT DOCUMENTS

EP          0241940           10/1987
EP          0523680           1/1993
WO      WO2006/059084         6/2006

OTHER PUBLICATIONS

Marchington, Robert F. et al: "High Throughput Photoporation of Mammalian Cells using Microfluidic Cell Delivery"; Conference of Lasers and Electro-Optics (CLEO) and Quantum Electronics and Laser Science Conference (QELS) May 16-21, 2010 San Jose, CA; IEEE, May 16, 2010, pp. 1-2.
(Continued)

*Primary Examiner* — Nathan Bowers
(74) *Attorney, Agent, or Firm* — Moore & Van Allen PLLC; W. Kevin Ransom

(57) ABSTRACT

A cell permeabilizing microfluidic system for permeabilizing one or more cells in a fluid flow. The system has a microfluidic channel for channeling at least one cell in a fluid flow and an optical source for generating a beam of light for permeabilizing the at least one cell, wherein the channel and the source are arranged so that the light beam and fluid flow are collinear in a permeabilization part of the channel and cells are permeabilized within the permeabilization part.

25 Claims, 8 Drawing Sheets

(51) Int. Cl.
*C12M 1/42* (2006.01)
*B01L 3/00* (2006.01)
*G01N 21/05* (2006.01)
*C12N 13/00* (2006.01)
*G01N 21/03* (2006.01)

(52) U.S. Cl.
CPC ........ *G01N 21/05* (2013.01); *B01L 3/502761* (2013.01); *G01N 2021/0346* (2013.01)

(56) References Cited

U.S. PATENT DOCUMENTS

| | | |
|---|---|---|
| 2002/0019052 A1 | 2/2002 | Nolan et al. |
| 2004/0080744 A1 | 4/2004 | Hobbs |
| 2005/0140971 A1 | 6/2005 | Yamaguchi et al. |
| 2008/0138876 A1 | 6/2008 | Ragsdale |
| 2009/0325217 A1* | 12/2009 | Luscher ............. G01N 15/1404 435/29 |
| 2010/0047761 A1* | 2/2010 | MacDonald ........... C12M 47/04 435/2 |
| 2010/0060892 A1 | 3/2010 | Beck et al. |
| 2011/0008817 A1 | 1/2011 | Durack |

OTHER PUBLICATIONS

Cran-McGreehin, Simon et al.: "Integrated monolithic optical manipulation"; Lab on a Chip; vol. 6, No. 9, Jan. 1, 2006, p. 1122-1124.
International Search Report for GB1110454.4, dated Oct. 17, 2011.
International Search Report for PCT/GB2012/000537, dated Sep. 20, 2012.

* cited by examiner

MICROFLUIDIC PHOTOPORATION

INTRODUCTION

The present invention relates to a system for the injection of "injection agents" that could include chemical agents, particulate matter (eg nanoparticles, quantum dots) or biological agents (eg DNA, RNA, proteins) into biological cells, through the use of an optical field for cell permeabilization in conjunction with a fluid flow.

BACKGROUND

The use of a focused laser beam to create a sub-micron diameter self-healing pore in the plasma membrane of a cell (photoporation/optoporation), for the selective introduction of membrane impermeable substances (optical injection/optoinjection) including nucleic acids (optical transfection), is a powerful technique most commonly applied to treat single cells. The membrane of a healthy cell is impenetrable to large polar molecules. The ability to overcome this barrier and inject a foreign material, such as nucleic acids (e.g. DNA, mRNA, interference RNA), a stain or a drug for example, into a living biological cell without damaging the integrity of the cell or the agent, is of interest to a wide range of applications in biology and medicine.

A diverse range of methods exist for permeabilizing the membrane of a cell for the insertion of foreign material including: the insertion of micron-sized pipettes (microinjection); application of electric fields (electroporation); ballistic insertion of coated nanoparticles (gene gun); transportation of therapeutic agents encapsulated in lipid- (lipofection) or polymer-based particles; viral delivery; pore formation or permeabilization using acoustic waves (sonoporation); and using laser fields to open a transient pore in the membrane (photoporation). Of these, photoporation has successfully been demonstrated on a wide range of both animal and plant cell types and has numerous advantages. However, photoporation approaches to date have been limited to low throughput, small-scale studies, as they typically require manual sequential dosing of individual cells.

One system that starts to address the issue of throughput in photoporation is described by Marchington et al. in Biomedical Optics Express 1, 2, 527 (2010). This system has a microfluidic chip that is used to deliver cells through a focused femtosecond laser beam for photoporation, enabling cells to be targeted in an automated approach. The beam is focused to a diffraction limited spot using an external microscope objective, and cells pass through the focus in an orthogonal direction to the direction of laser propagation. Doing this allowed throughputs of one cell per second to be achieved. However, due to the requirement for the cells to be exposed to the beam for 1-10's of milliseconds, the throughput is still limited.

SUMMARY OF INVENTION

According to the present invention, there is provided a cell permeabilizing microfluidic system for permeabilizing one or more cells in a fluid flow, the system comprising a microfluidic channel for channeling at least one cell in a fluid flow and an optical source for generating a beam of light for permeabilizing the at least one cell, wherein the channel and the source are arranged so that the light beam and fluid flow are collinear in a permeabilization part of the channel and cells are permeabilized within the permeabilization part.

Because the light beam and fluid flow are collinear, the laser dose required for photoporation can be extended along the entire interaction length of the laser field rather than being confined to a small interaction volume. This allows for an increased fluid flow rate and thus throughput. A further advantage is that cells can be passed sequentially through a light field for continuous poration. This can be conducted in an automated, high-throughput manner for the injection of large numbers of cells, with the high efficiencies and post-injection viabilities possible using photoporation.

The microfluidic system may have cell guiding means for guiding the cells in a confinement region contained within the fluid flow in the permeabilization part. Preferably, the cell guiding means are based on hydrodynamic focusing. The cell guiding means may comprise a three-dimensional nozzle. The light beam may extend over a volume that includes the confinement region.

Preferably, the fluid channel has an "L-bend" or "S-bend" or "U-bend", and the optical source is positioned at a bend.

The channel and the optical source may be arranged so that the light beam is parallel to the channel walls.

The channel and the optical source may be arranged so that in the permeabilization part the cell flow is moving in a direction opposite to the direction of propagation of the light beam.

The microfluidic system may have means of varying the light beam intensity profile. Such means may include an axicon lens and/or a spatial light modulator. The means of varying the light beam intensity profile may be used for generating a non-diffracting light beam such as a Bessel beam. Preferably the Bessel beam is propagation invariant along the length of the permeabilization part of the channel. Due to its extended propagation-invariant focal spot, the Bessel beam can be positioned along the length of the S-bend, for high flow rate photoporation. The central core of the Bessel beam self-heals around an obstruction. This means that multiple cells within the flow can be porated/permeabilized simultaneously (where any one cell aligned with the central core is considered an obstruction).

The microfluidic system may have one or more inlets provided for introducing one or more additional fluids into the micro fluidic channel. The one or more inlets may be positioned to allow one or more additional fluids to be introduced into the micro fluidic channel before the permeabilization channel.

The light may be coupled into the permeabilization channel using an optical fiber and/or a waveguide.

The channel may have a square cross-section or a circular cross-section or a rectangular cross-section. The channel may have cross sectional dimensions in the range of 1-500 μm, for example, 10-500 μm, optionally 50-100 μm. The microfluidic channel and/or optical source may be formed on-chip, forming an integrated on chip device.

The optical source may be arranged to provide a light beam that is such that cell function is preserved after permeabilization.

As non-limiting examples, the system may be used to permeate the membranes of biological cells (animal, plant and fungi), bacteria, sections of tissue or attached multiple cells, multicellular microscopic living organisms, extracellular vesicles (e.g. exosomes), subcellular organelles (e.g. mitochondria, nuclei, chloroplasts, endosomes, vesicles), lipid and artificial micelles, lipid droplets, and artificial or modified versions of any of these listed particles. The size range of particles that could be permeated could range from 10's nanometers to 1's millimeters.

According to the present invention, there is provided a method for permeabilizing one or more cells in a fluid flow comprising exposing the cells in the fluid to a light beam that is collinear with the direction of fluid flow. Preferably, the light beam is a Bessel beam.

The method may comprise introducing one or more additional fluids into the fluid flow prior to light exposure.

BRIEF DESCRIPTION OF THE DRAWINGS

Various aspects of the invention will now be described by way of example only and with reference to the accompanying drawings, of which.

SPECIFIC DESCRIPTION

Figure 1:
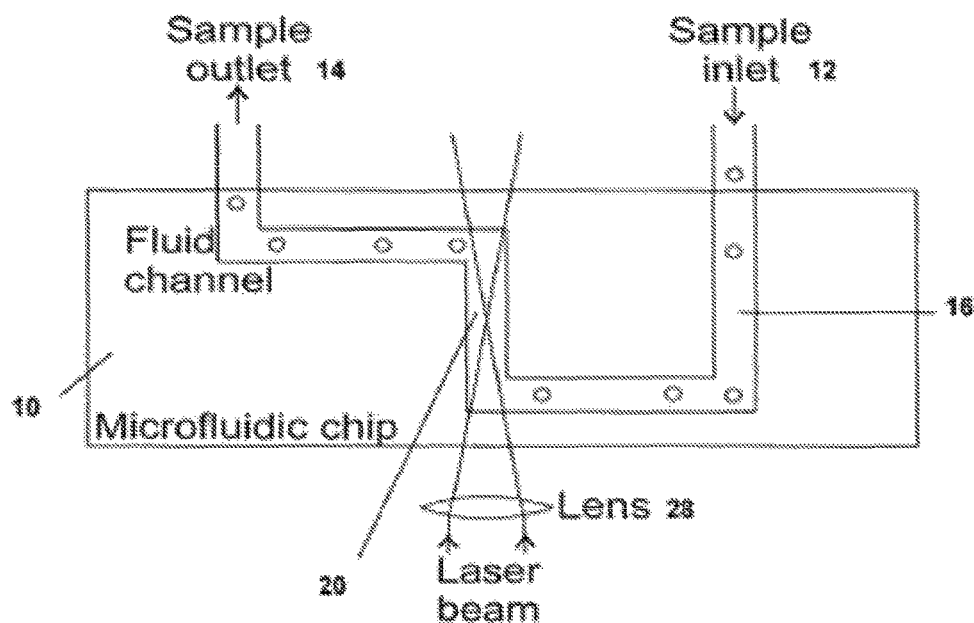
FIG. 1 is a schematic view of a photoporation system with a microfluidic chip with a s-bend channel geometry.

FIG. 1 shows a microfluidic chip 10 that has a sample inlet 12, a sample output 14 and a fluid flow channel 16 that has a s-bend geometry that causes the direction of fluid flow to change as the fluid moves through the channel 16. At one corner of the channel 16, a lens 18 is used to focus or relay an optical field into a poration section 20 of the fluid channel 16. The laser beam is coupled into the poration channel 20 collinear to the direction of fluid flow. A fluid medium containing the cells and possibly an agent that is to be injected into the cells is flowed through the fluid channel 16. Once in the poration channel 20, the laser beam is used to permeabilize the membranes of cells as they move towards the sample outlet 14.

Any suitable laser beam can be used in the arrangement of FIG. 1. However, in a preferred embodiment, a Bessel beam is used. Bessel beams are non-diffractive and so propagation invariant. They are also self-healing, and so if they are partially obstructed at one point, they will re-form at a point further down the beam axis.

Figure 2:
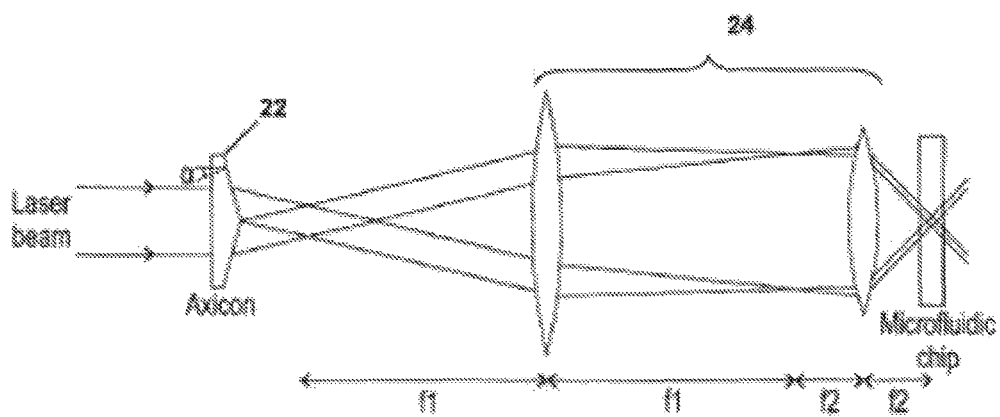
FIG. 2 is a schematic view of an optical setup for producing a Bessel beam using an axicon lens.

FIG. 2 shows an optical arrangement for relaying a Bessel beam. The Bessel beam is generated by an axicon lens 22 that has a cone angle α. The relay optics 24 has two lenses with focal lengths f1 and f2. The lenses are provided to relay and re-size the Bessel beam within the microfluidic chip 10. In particular, in the arrangement shown in FIG. 2, the Bessel beam core is reduced by the factor f2/f1. The combination of the lenses and the cone angle, α, determine the final core radius of the Bessel beam and its propagation-invariant length.

Figure 3:
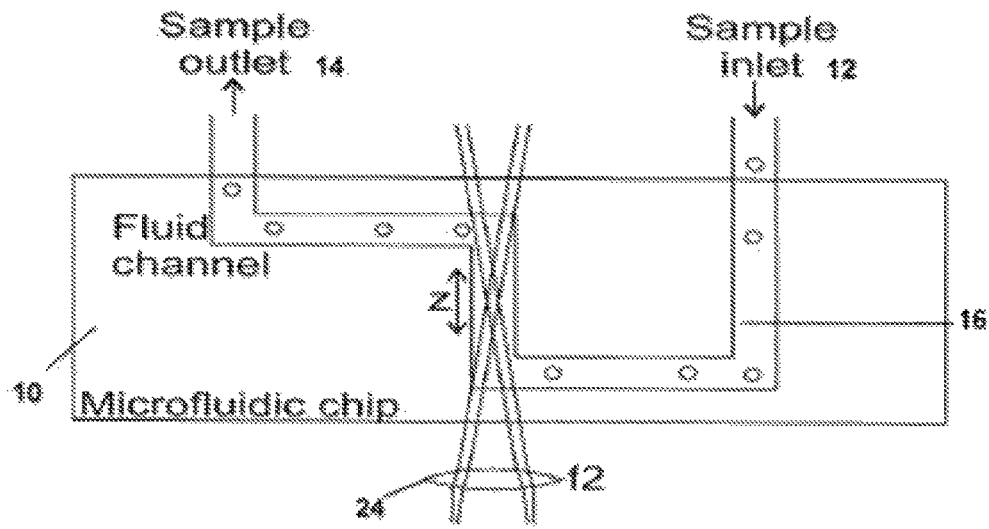
FIG. 3 is a schematic view of a photoporation system with a microfluidic chip with a s-bend channel geometry and a lens for relaying a Bessel beam into the channel.

FIG. 3 shows the last lens f2 in the relay system in FIG. 2 focusing a Bessel beam into the poration channel 20 of an s-bend microfluidic chip. The distance, z indicates the non-diffracting length of the Bessel beam core. The distance z, divided by the flow velocity in the region of the beam core gives a measure of the photoporation dose duration. By extending the distance z, the flow rate can be increased.

Figure 4:
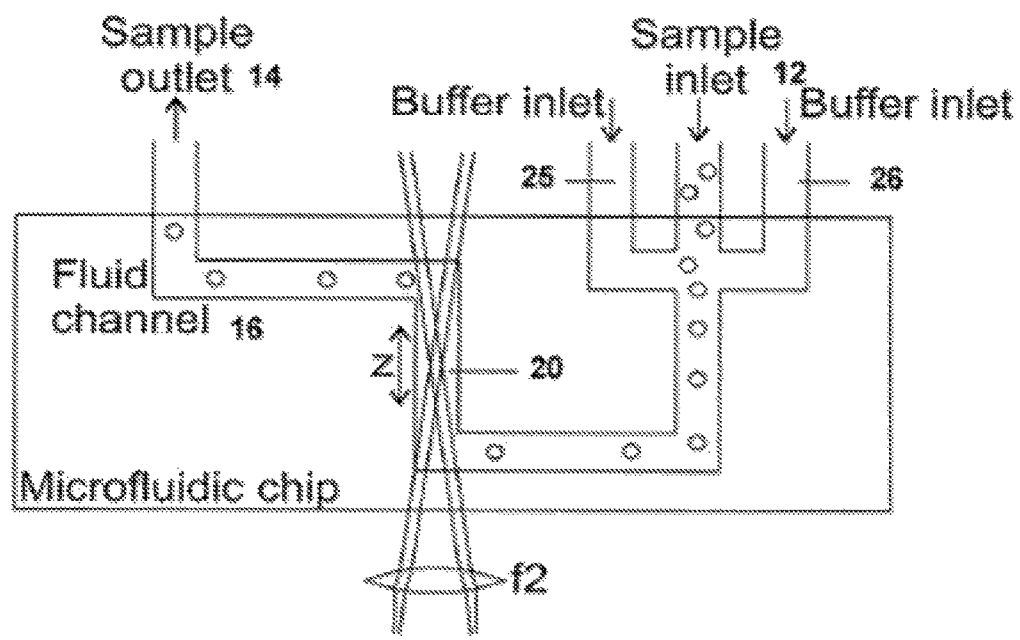
FIG. 4 is a schematic view of another photoporation system with a microfluidic chip with a s-bend channel geometry and a lens for relaying a Bessel beam into the channel.

FIG. 4 shows a microfluidic poration system similar to those previously described, but with two buffer inlets 25, 26 that feed into the s-bend downstream from the sample inlet 12, but before the poration channel 20. The buffer inlets 24, 26 allow one or more buffer flows to be incorporated to provide flow focusing (hydrodynamic focusing) of the sample to confine the cells to the centre of the channel 16 in one or two dimensions. This allows hydrodynamic focusing to provide confinement of the sample in one or two dimensions. Confinement could be provided by combining multiple fluid streams, as shown, or through the use of electric fields. The lens f2 relays a Bessel beam into the poration channel 20 with core diameter invariance over the length z.

Figure 5:
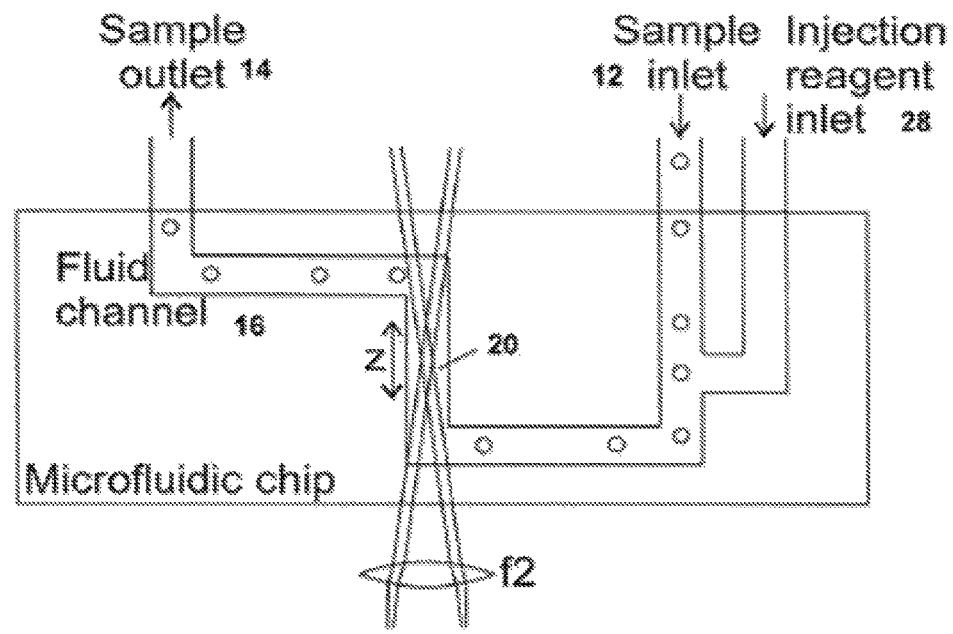
FIG. 5 is a schematic view of a further photoporation system with a microfluidic chip with a s-bend channel geometry and a lens for relaying a Bessel beam into the channel.

FIG. 5 shows yet another microfluidic poration system similar to those previously described, but with an injection reagent inlet 28 for allowing a reagent to be injected into the s-bend downstream from the sample inlet 12, but before the poration channel 20. As before, the lens f2 relays a Bessel beam into the chip 10, with core diameter invariance over the length z. Depending on the diffusion constant of the injection agent, on-chip mixing elements may be required for homogenous mixing of the agent with the cells.

Inlets for other agents, such as fixatives, viability stains, drugs, fluorescent dyes, antibiotics, or multiple injection agents, for example, could be included. An inlet for an immiscible liquid, such as silicone or mineral oil, could be included for encapsulating cells within droplets, e.g. water based droplets (containing one or more cells) within an oil-based medium. Such a droplet system could enable reduced reagent consumption, precise delivery of reagent concentrations to within droplets and improved reagent homogeneity, for instance. By controlling the droplet spacing, the spacing of multiple cells within the permeabilization part of the channel could be managed.

Figure 6:
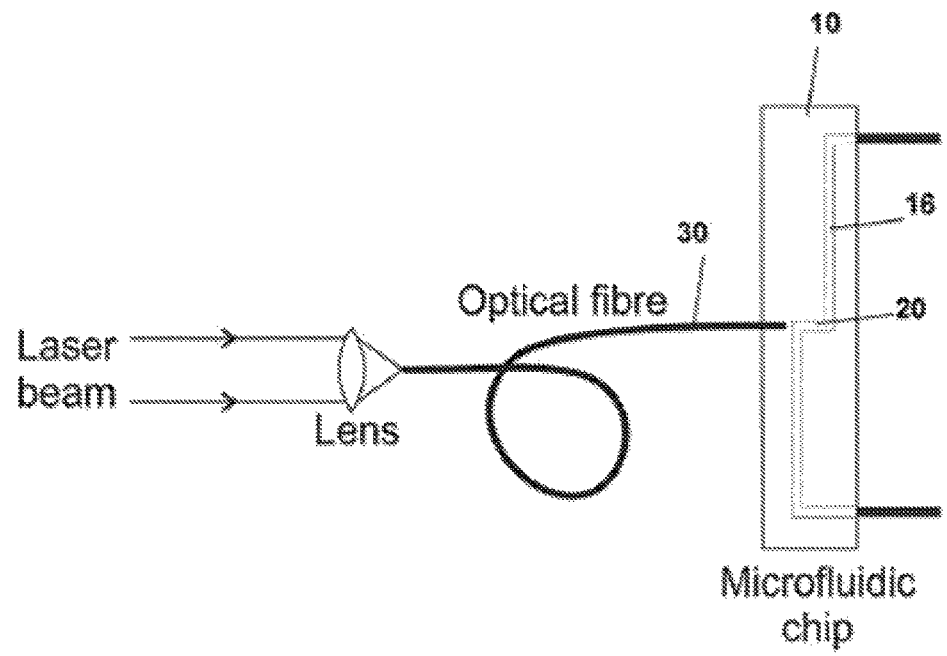
FIG. 6 is a schematic view of yet another photoporation system with a microfluidic chip with a s-bend channel geometry, with an optical fiber delivery system.

FIG. 6 shows an optical fiber 30 for delivering laser light to a s-bend microfluidic chip 10. The laser beam is coupled to the optical fiber 30, which delivers light to the chip 10. The fiber 30 delivers the light directly to the microfluidic channel 16. Alternatively, further beam shaping and/or waveguiding elements may be provided on-chip to shape and/or guide the light to the poration channel 20. A lens 32 could be used to couple the light to the fiber, or alternatively a pigtailed laser could be used (where the fiber is attached to the laser facet). In another embodiment, waveguides are included on chip for delivering light to multiple regions on the chip, and beam shaping elements are used to create Bessel beams, or multiple focal spots.

Figure 7:
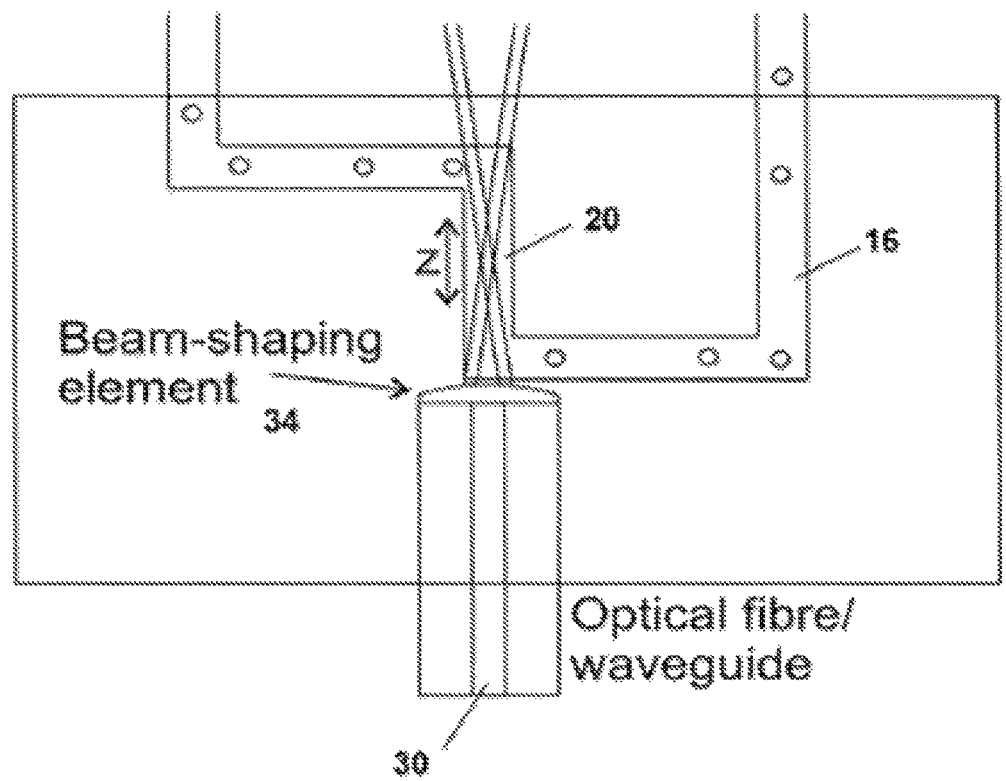
FIG. 7 is a schematic view of a photoporation system with a microfluidic chip with a s-bend channel geometry, with an optical fiber delivery system and a beam shaping element.

FIG. 7 shows a chip 10 with an optical fiber 30 for delivering light to the chip 10 and a beam shaping element 34 between the fiber 30 and the fluid channel 16 for producing various beam shapes. The fiber 30 could be replaced with a waveguide, allowing for more complicated optical circuits, such as delivering the light to multiple regions on the chip. In this case, an optical fiber may be used to deliver light from the laser to the waveguides.

In all of the examples described above, the dimensions of the microfluidic channel should be larger than the particles or cells to be photoporated to prevent blockages occurring. Increasing the channel size reduces the shear stresses on the cells, but also reduces the likelihood of the cells overlapping with the photoporation beam, thus increasing the requirement for cell focusing. The maximum size for the channel is determined by the Reynolds number. A low Reynolds number is desirable for obtaining a well determined turbulent-free laminar flow of cells, for controlled laser dosing. Channel dimensions of 50-100 µm are appropriate for photoporating mammalian cells with diameters up to 25 µm. If cell confinement is incorporated, through hydrodynamic focusing, for instance then the size of the confined cell flow (through changing the ratio of flow rates of the sample and buffer) rather than the overall channel dimension is important.

The size of the optical beam to be delivered to the flow channel is also a consideration. For the case of the Bessel beam, the cross sectional channel dimensions should be greater than that of the diameter of the outer-most Bessel beam ring, so as not to diffract and thus truncate the propagation length. Demagnifying the Bessel beam could allow it to fit into a smaller channel, but this is at the expense of propagation length and core diameter.

The cross-section profile of the flow channel typically is circular or square. A circular profile produces a radially-symmetric parabolic flow profile. A similar flow profile is created using the square flow channel. A rectangular profile causes the cross-sectional flow profile to tend closer to the Hele-Shaw "plug-like" flow, which could allow many cells to flow in parallel at near-identical fluid flow velocities. Combined with a photoporation laser illuminating along a plane, this could provide very large laser-dosing throughputs.

Regarding the side profile of the fluid flow channel, at the entrance point of the beam this should be flat to allow the beam to enter unimpeded, other than losses due to Fresnel reflections (that could optionally be minimized with appropriate anti-reflection coatings and/or index matching).

Confinement of the cells to a region (e.g. center) of the flow channel, for optimal overlap between the laser and moving cells, could be achieved using a number of methods, such as hydrodynamic focusing, as discussed above. Other techniques for cell confinement may be based on Dean flow inertial effects; electric-field driven focusing, such as dielectrophoresis; or Bernoulli-driven force towards the center of the flow channel due to the parabolic flow profile, for example.

The fluid flow can be driven by one of a number of available pumps or on-chip methods. This could be external fluid pumping using syringe pumps, peristaltic pumps, pressure-driven pumps, or gravity feeds (syphon effect), or on-chip driven flow could be generated using electric fields for electrokinetic driven flow of the fluid and/or the particles. Optical fields could be used to drive particles around the chip using scattering and/or gradient forces, which could be enhanced with dielectric particles for increasing the overall contrast between the cell (and dielectric particle) and the surrounding medium. The direction of fluid flow and the direction of propagation of the optical beam could be the same or opposite.

A number of different optical sources can be used for the photoporation process, for example a femtosecond laser source, such as a Titanium:Sapphire laser, for delivering femtosecond doses to cells. However, a wide range of other sources have been demonstrated to photoporate cells successfully, including continuous wave, picosecond, and nanosecond sources. Indeed, any source adapted to provide a beam that can be used to form a self-healing pore in a cell could be used.

Femtosecond sources are thought to interact with the cell membrane through a multi-photon process, and as such provide a high degree of confinement, with minimal collateral damage to the cell, and for minimal dose duration. Typical parameters for femtosecond photoporation are one or more 1-100's millisecond doses of light at 780-800 nm, with a pulse duration of 50-500 fs at a 80 MHz repetition frequency, with an average power of between 1 mW and 100 mW, for example 40-100 mW contained within a 1-2 µm focal spot (central core) on the cell membrane. For the case of the Bessel beam, the overall optical power required is multiplied by the number of rings in order to obtain a comparable optical power in the central core. Ideally, for pulsed femtosecond sources, the average power of the central core of the Bessel beam should be in the region of 1 mW to 100 mW.

The dose duration is the time that the cell resides within the optical field, and is related to the fluid flow velocity, but is also a function of the optical power and the exact beam focal spot size (central core size). The exact optical dose and power must be determined empirically for a given system, injection agent, and cell type. If the dose duration or the optical intensity is too low, permeabilization may not occur, or if either is too high, damage to the cell may occur leading to cell death. Hence, the dose duration and/or the optical intensity/power are selected to allow permeabilization but avoid cell damage. Optionally, a shutter is included between the laser source and the microfluidic channel, allowing the laser doses to be time-gated, for further control of the photoporation effect. Non-laser sources, such as LED's or discharge lamps could also satisfy the required optical parameters for photoporation. For example, a blue/violet LED could be used. In this case, the average beam power could be in the range 1 mW to 10 mW with an irradiation dose of the order of 0.1-5 seconds. All of the sources mentioned could be used in continuous wave mode.

Targeting of the cells with the laser can be achieved in a number of ways. Controlling the confluency of the cell sample would enable cells to enter the permeabilization channel one at a time, with the optical field being on continuously. Alternatively, a triggering mechanism could be used. This could use image processing, fluorescence excitation and detection, or light scattering; to detect the presence of a cell. Once the cell is detected then the photoporation beam could be triggered with a suitable time delay to target the detected cell. If a Bessel beam is used, the self-healing property of the beam could be used for allowing larger numbers of cells to pass through the permeabilization channel, without them causing distortion of the beam that would otherwise impair permeabilization. As such the system could be operated in three modes: the porating beam always being on, so that when cells move into the porating channel they are immediately exposed; the beam could be triggered on detection of a cell; or with adequate control over the cell spacing, a specific triggering rate could be set to correspond with the frequency of cells passing into the porating channel.

Beam shaping could be used to alter the profile of the optical field within the channel. This could include using a diffractive optic element for multiplexing the beam to produce multiple focal spots, and lenses for focusing. Fresnel lenses could be used as they are highly compact and more easily fabricated in lab-on-a-chip structures. Multiple lenses could be positioned along a length of channel to produce an array of focal spots.

The system of the invention has been used successfully to inject cells with a dye. High-throughput optical injection of mammalian cells was demonstrated on Human promyeloctic leukemia cells (HL-60) and Chinese hamster ovary cells (CHO-K1). The injection efficiency was determined using the cell membrane impermeable dye, propidium iodide (PI), and subsequent cell viability by using Calcium AM (CAM).

HL-60 cells were cultured in RMPI-1640 (Sigma Aldrich) and CHO-K1 cells were cultured in Modified Eagle's Medium (MEM). In addition to culturing medium, 10% foetal calf serum (FCS, Globepharm), 20 µgml$^{-1}$ streptomycin (Sigma Aldrich) and 20 µgml$^{-1}$ penicillin were used in preparation for both cell lines. The cells were cultured in T25 flasks and incubated in a humidified atmosphere of 5% $CO_2$ at 37° C. These cells were routinely sub-cultured three times per week.

Propidium iodide is a nucleic acid stain and is membrane impermeable for living, viable cells. It is taken up by cells where the membrane has been compromised and subsequently binds to DNA where upon it exhibits a 20-30 fold increase in fluorescence with an emission maximum at 617 nm. PI uptake is present in both optically injected cells and otherwise compromised cells, i.e. cells that are dead or damaged and have a membrane that is permeable relative to their healthy counterparts. Calcium-AM (CAM) was used to test cell viability. CAM is a membrane permeable stain which is converted to calcein within the cell and fluoresces with an emission peak at 530 nm. The microfluidic system was filled with opti-MEM containing the injectant, PI at a concentration of 1.5 µM. The opti-MEM was warmed to 37° C. before use in the chip to lower the chances of gas bubble formation.

In the case of HL-60 cells, which grow in suspension, 100-400 µL of confluent cells were aliquoted from stock into a 1.5 ml micro-centrifuge tube. The micro-centrifuge tube was topped up with opti-MEM and centrifuged in a micro-centrifuge at 500 rcf for 5 minutes. The cells were rinsed again in fresh opti-MEM before being suspended finally in opti-MEM containing PI (1.5 µM). The cell confluency was measured at this point using a hemocytometer before being loaded into a 25 µL syringe. A typical cell density of $1.2 \times 10^6$ cells/mL was used in each run. Two cell culture dishes containing 400 µL of opti-MEM were prepared. 7.5 µm of the final cell suspension was added to one dish for the bench control. The other dish was used to collect cells from the outlet of the microfluidic system.

Figure 8:
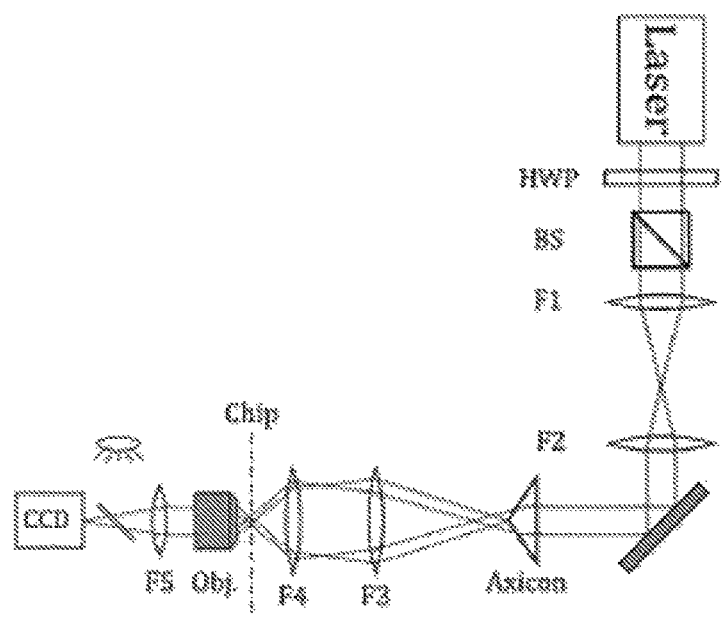
FIG. 8 is a schematic view of an optical setup for microfluidic photoporation.
Figure 9:
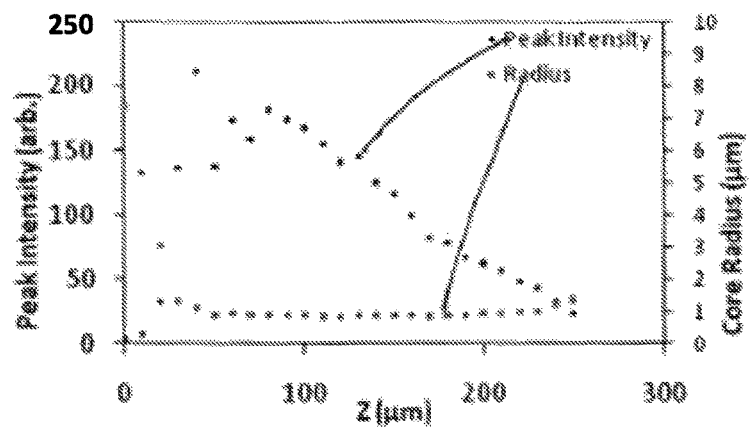
FIG. 9 shows plots of the peak intensity and core size against distance for the Bessel beam obtained with the setup of FIG. 8.

The experimental setup is shown in FIG. 8. A modelocked Ti:Sapphire femtosecond laser (Chameleon, Coherent, Inc., λ=800 nm, 140 fs pulse duration at a 80 MHz repetition rate) was used for optical injection. A half-wave plate and a polarising beam splitter were used in conjunction to attenuate the laser beam to the desired power. An axicon with an opening angle of 5° was used to generate a Bessel beam. By using an 8× demagnifiying telescope, the Bessel beam was generated with a central core width of 1.9 µm and a propagation length of 170 µm as shown in FIG. 9. The efficiency of the optical system was measured to be 80.2% from before the first telescope to the sample plane.

A microfluidic chip was positioned in the path of the Bessel beam in such a way that the Bessel beam coupled into the center of the poration/permeabilization section of the microfluidic channel collinear to the direction of fluid flow. In the poration/permeabilization section, the cells are guided along the channel and along the length of the Bessel beam core. In this section, the cell flow moves in a direction opposite to the direction of propagation of the laser beam.

Figure 10:
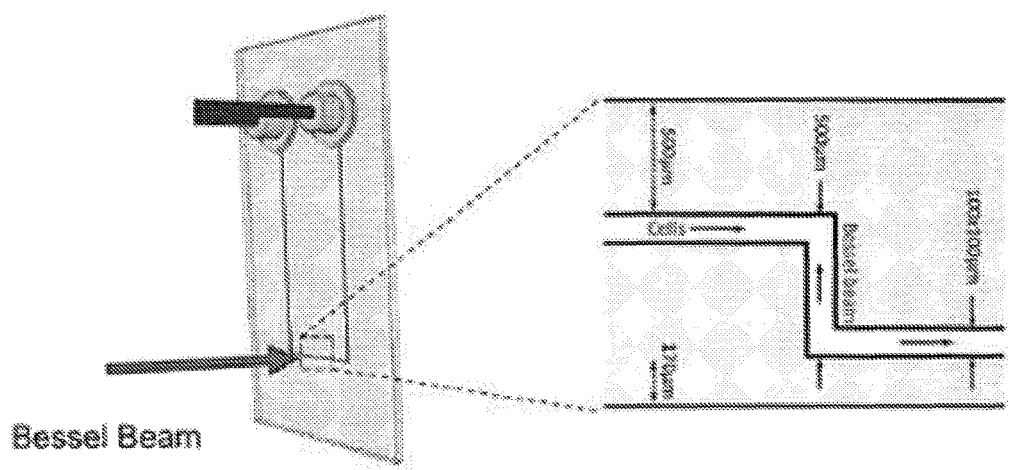
FIG. 10 is a schematic view of microfluidic chip with a poration S-bend channel.

FIG. 10 shows the microfluidic chip. It has a 500 µm long poration/permeabilization section situated beyond a 170 µm thick window through which the non-diffracting Bessel beam is directed. The chip was created from three thermally bonded plates with channel dimensions of 100 µm×100 µm (Translume, Inc.). The channels were square in cross-section throughout the chip, except at the inlet and outlet port where a circular indentation, 250 µm deep, was included to accommodate the diameter of the PEEK tubing (Upchurch 1561). Nanoports (Upchurch) were fixed to the inlet and outlet to connect microfluidic tubing with minimal dead volumes. The chip was held in a vertical position such that the kink in the channel was orientated parallel to the optical bench and to the Bessel beam. A custom built microscope was used to image along the photoporation channel and to aid with alignment.

Figure 11:
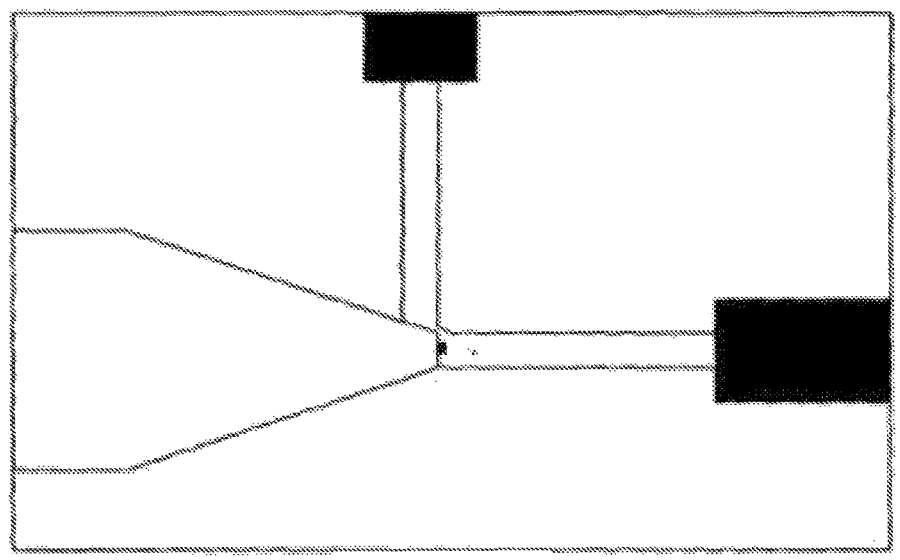
FIG. 11 shows a cutaway view of the inside of a T-junction aligning a sample capillary (left) within a buffer flow (top)

Two dimensional hydrodynamic focusing was achieved using a three-dimensional nozzle constructed from commercially available parts (A. Terray and S. J. Hart, Lab on a chip, 2010, 10, 1729-31). The device was constructed by fixing a silica capillary (360 µm OD, 50 µm ID) within a microferrule using a two-part epoxy. The capillary was then housed within a T-junction from a micro-metering valve assembly. A cutaway view of the flow focusing junction is shown in FIG. 11. As the capillary extends beyond the junction and is narrower than the surrounding channel, a sheath flow is free to surround the capillary nozzle. PEEK tubing was connected to the remaining arm of the junction where the focused sample was delivered to the microfluidic chip.

The nozzle assembly allows the formation of a core flow, containing the sample cells and guided within the outer sheath flow. By adjusting the relative flow rates of the core and sheath flow, the degree of confinement of the sample can be controlled. The velocity of particles along the channel can also be controlled by changing the combined flow rate. The core and sheath flows were controlled using two syringe pumps (Harvard Apparatus, Pico Plus). A 25 µL and a 100 µL gastight syringe (Hamilton) were used with the syringe pumps to control the sample and buffer flow respectively.

Figure 12:
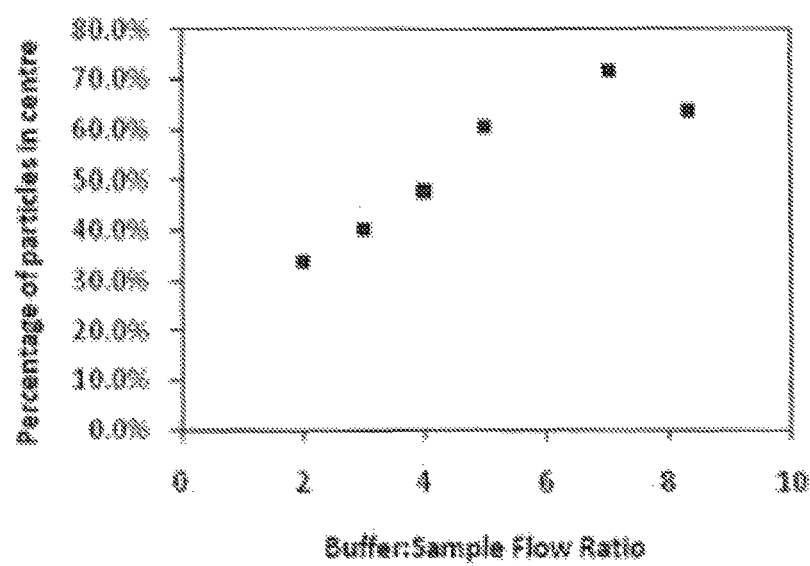
FIG. 12 shows a plot of the percentage of particles passing through the central region of the channel (within 15 um) against the buffer-sample flow ratio.
Figure 13:
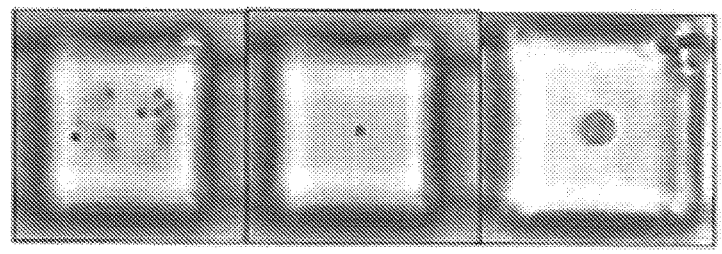
FIG. 13 shows beads in a microfluidic channel with no buffer flow (left), with a buffer/sample flow ratio of 210:30 ulhr$^{-1}$.

The hydrodynamic focusing device was tested with 4 µm polymer beads in solution. A range of flow ratios were tested, as shown in FIGS. 12 and 13. Using a high-speed camera (Fastec Imaging), a short segment of video was recorded. The videos were then analyzed to record the position of each polymer sphere relative to the center of the channel. This data was then used to deduce the likelihood of cells (typically ~20-25 µm in diameter) passing through the center of the channel and thus through the core of the Bessel beam. Without hydrodynamic focusing, 7% of the beads flowed within 15 microns of the channel center. Increasing the core/buffer flow ratio up to 1:7 showed a 10-fold increase with 72% of particles passing through the same region (FIG. 12).

For each optical injection experiment, the microfluidic system was flushed with 5% decon 90, milli-Q filtered water and 70% ethanol before it was dried with filtered air using the peristaltic pump. The chip and tubings were filled with opti-MEM solution containing PI using the peristaltic pump. This pump was then disconnected and replaced with a syringe injection port and 100 μL syringe containing additional opti-MEM solution for the buffer flow. Care was taken so as to not introduce air bubbles into the system.

Once the sample syringe containing cells was in position, the syringe pumps ran at a fixed flow rate (30 μL hr$^{-1}$ for the sample and 210 μl hr$^{-1}$ for buffer flow) and the chip was exposed to the Bessel beam. Typically one minute after starting the syringe pump, cells were visible flowing through the photoporation region of the chip with good localisation in the center of the channel. A glass-bottomed cell culture dish (FluoroDish, World Precision Instruments, Inc.) containing opti-MEM was used as a collection vessel at the outlet. After a further 15 minutes, the pumps and laser were turned off.

Once cells passed through the microfluidic system for fifteen minutes, they were collected and checked for a positive propidium iodide signal. The fluorescence of the cells was observed using a mercury lamp with a TRITC filter (Nikon). Approximately 200 cells per dish were counted. To check the viability of the cells, Calcium-AM was added to each dish at a concentration of 1 μM. The cells were returned to the incubator for 20 minutes before checking for cell viability using a FITC filter cube. In addition to a control dish on the bench, experimental runs were conducted with the absence of the Bessel beam to confirm the injection of PI was an optical effect rather than due to shear stresses inflicted by the microfluidic system.

Figure 14:
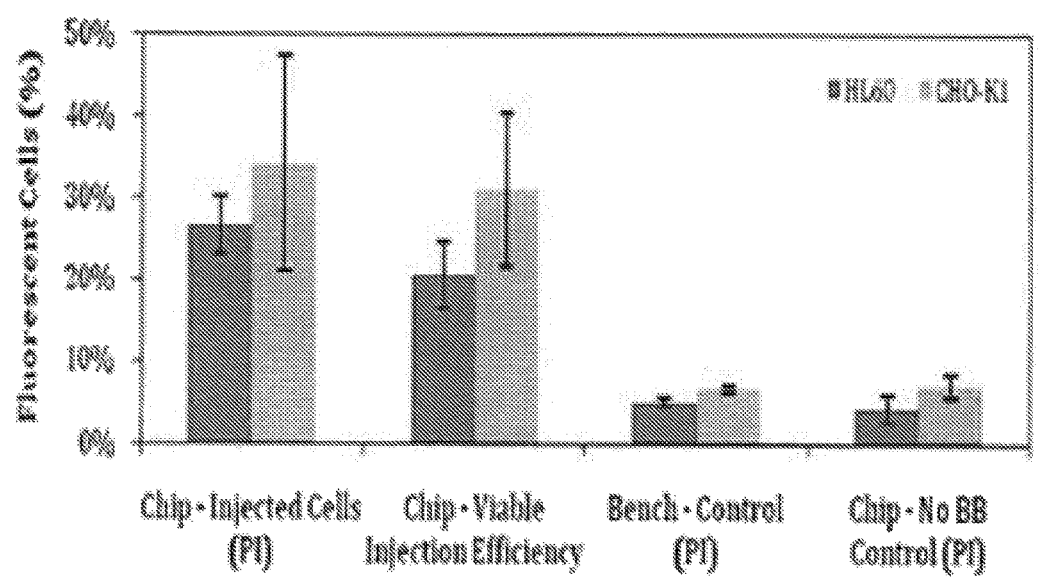
FIG. 14 shows the optical injection efficiencies of HL-60 cells with propidium iodide.

FIG. 14 shows the optical injection efficiencies of HL-60 and CHO-K1 cells with propidium iodide. As noted above, approximately 200 cells were counted in each sample to obtain the percentage of cells expressing PI. Viable injection is the injection efficiency corrected for cell viability. The error bars are the standard error of the mean (N=10 for HL60, N=3 for CHO-K1).

Figure 15:
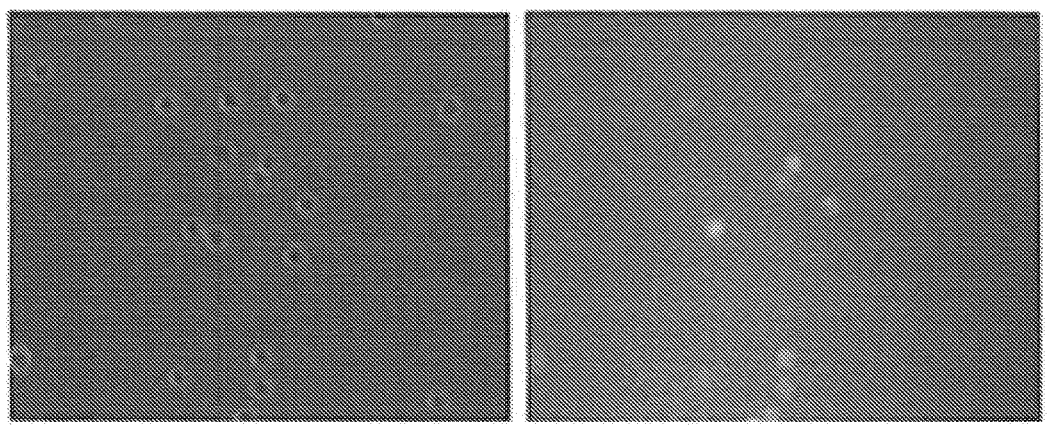
FIG. 15 shows the phase contrast image of treated HL60s (left) and PI fluorescence observed from the same cells (right).

At a constant flow rate (30 μL hr$^{-1}$ for the sample flow and 210 μL hr$^{-1}$ for the buffer flow), cell velocity was measured to be 7.4 mm s$^{-1}$ in a straight segment of channel. For the HL-60 cells, typically in the region of 9000 cells were collected giving an average throughput of 10 cells/s. This corresponds to a potential dose time, the time taken to traverse the propagation length of the Bessel beam, of approximately 23 ms. Under these conditions, 26.6±3.6% of cells exhibited PI fluorescence compared to 5.0±0.5% of the bench control. There was no significant difference observed between the bench control and with cells flowed through the chip in the absence of the Bessel beam. After correcting for the viability of the cells after flowing through the chip, the viable injection efficiency was found to be 20.4±4.2%. FIG. 15 shows a phase contrast image of the treated HL60 cells (left) and the PI fluorescence observed from the same cells (right).

CHO-K1 cells were also successfully optically injected using this microfluidic system. As the CHO cells are an adherent cell line, an additional step in cell preparation is required to create a cell suspension. Cells were suspended by adding 1 mL of Trypsin-EDTA and incubating cells for 5 minutes. This suspension was then rinsed with opti-MEM through centrifugation as previously described. Under the same microfluidic flow and laser conditions, 34.2±13.1% injection efficiency was achieved with a corrected efficiency of 31.0±9.5%.

The use of an experimental setup having a poration/permeabilization section where, the cells flow along a "non diffracting" beam, allows for higher flow speeds to be used whilst maintaining an adequate dose for the optical injection of cell membrane impermeable substances. This has led to an order of magnitude increase in throughput compared to previous orthogonal approach for microfluidic photoporation (R. F. Marchington et al, Optics Express, 2010, 1, 33-36). As the dose time is governed by the velocity of the cell through the channel, this can be readily changed by altering the overall flow rates whilst maintaining good confinement within the central region of the channel.

A skilled person will appreciate that variations of the disclosed arrangements are possible without departing from the invention. For example, other functionalities could be incorporated on the same chip as the poration optics. In particular, on-chip fluorescence could be used to distinguish successfully injected cells or check for cell viability (using a viability stain such as propidium iodide or calcein AM for instance, and could optionally be introduced on-chip). Fluorescent-activated sorting (FACS) or other sorting techniques could be used to fractionate cells before or after the photoporation procedure. Fluid mixing and/or filtering regions on the chip may also be provided. Accordingly, the above description of the specific embodiment is made by way of example only and not for the purposes of limitation. It will be clear to the skilled person that minor modifications may be made without significant changes to the operation described.

The invention claimed is:

1. A cell permeabilizing microfluidic system for permeabilizing one or more cells in a fluid flow, the system comprising:
    a microfluidic channel for channeling at least one cell in a fluid flow; and
    an optical source for generating a beam of light for permeabilizing the at least one cell,
    wherein the microfluidic channel and the optical source are arranged so that the light beam and fluid flow are collinear in a permeabilization part of the microfluidic channel and cells are permeabilized within the permeabilization part, and the light beam is non-diffracting and so propagation invariant in the permeabilization part of the microfluidic channel.

2. The microfluidic system as claimed in claim 1 comprising cell guiding means for guiding the cells in a confinement region contained within the fluid flow in the permeabilization part.

3. The microfluidic system as claimed in claim 2, wherein the cell guiding means are based on hydrodynamic focusing.

4. The microfluidic system as claimed in claim 3, wherein the cell guiding means comprises a three-dimensional nozzle.

5. The microfluidic system as claimed in claim 2, wherein the light beam extends over a volume that includes the confinement region.

6. The microfluidic system as claimed in claim 1, wherein the microfluidic channel has a bend and the light beam is coupled into the microfluidic channel at the bend.

7. The microfluidic system as claimed in claim 1, wherein the microfluidic channel is L-shaped or S-shaped or U-shaped.

8. The microfluidic system as claimed in claim 1, wherein the microfluidic channel and the optical source are arranged so that the light beam is parallel to the microfluidic channel walls.

9. The microfluidic system as claimed in claim 1, wherein the microfluidic channel and the optical source are arranged so that, in the permeabilization part, the cell flow is moving in a direction opposite to the direction of propagation of the light beam.

10. The microfluidic system as claimed in claim 1 further comprising means of varying the light beam intensity profile.

11. The microfluidic system as claimed in claim 10, wherein the means of varying the light intensity profile include an axicon lens.

12. The microfluidic system as claimed in claim 10, wherein the means of varying the light intensity profile include a spatial light modulator.

13. The microfluidic system as claimed in claim 1, wherein the non-diffractive light beam is a Bessel beam.

14. The microfluidic system as claimed in claim 13, wherein the Bessel beam is propagation invariant along the length of the permeabilization part of the microfluidic channel.

15. The microfluidic system as claimed in claim 1, wherein one or more inlets are provided for introducing one or more additional fluids into the microfluidic channel.

16. The microfluidic system as claimed in claim 15, wherein the one or more inlets are positioned to allow one or more additional fluids to be introduced into the microfluidic channel before the permeabilization part of the microfluidic channel.

17. The microfluidic system as claimed in claim 1, wherein light is coupled into the permeabilization part of the microfluidic channel using an optical fiber and/or a waveguide.

18. The microfluidic system as claimed in claim 1, wherein the microfluidic channel has a square cross-section or a circular cross-section or a rectangular cross-section.

19. The microfluidic system as claimed in claim 1, wherein the microfluidic channel has cross sectional dimensions in the range of 1-500 µm.

20. The microfluidic system as claimed in claim 1, wherein the microfluidic channel is formed on-chip.

21. The microfluidic system as claimed in claim 1, wherein the microfluidic channel and optical source are on-chip forming an integrated on chip device.

22. The microfluidic system as claimed in claim 1, wherein the microfluidic system is arranged so that cell function is preserved after permeabilization.

23. A method for permeabilizing one or more cells in a fluid flow in a microfluidic channel comprising exposing cells in a permeabilization part of the microfluidic channel to a light beam that is collinear with the direction of fluid flow in the permeabilization part of the microfluidic channel to thereby permeabilize the cells, wherein the light beam is non-diffracting and so propagation invariant in the permeabilization part of the microfluidic channel.

24. The method as claimed in claim 23, wherein the light beam is a Bessel beam.

25. The method as claimed in claim 23 further comprising introducing one or more additional fluids into the fluid flow prior to light exposure.

* * * * *